US008557532B2

(12) United States Patent
Lessnick et al.

(10) Patent No.: US 8,557,532 B2
(45) Date of Patent: Oct. 15, 2013

(54) DIAGNOSIS AND TREATMENT OF DRUG-RESISTANT EWING'S SARCOMA

(75) Inventors: Stephen L. Lessnick, Salt Lake City, UT (US); Wen Luo, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 161 days.

(21) Appl. No.: 12/871,603

(22) Filed: Aug. 30, 2010

(65) Prior Publication Data
US 2012/0053136 A1 Mar. 1, 2012

(51) Int. Cl.
*G01N 33/574* (2006.01)
*G01N 33/53* (2006.01)
*G01N 33/00* (2006.01)
*C12Q 1/00* (2006.01)
*C12Q 1/68* (2006.01)

(52) U.S. Cl.
USPC ............ 435/7.23; 435/4; 435/6.12; 435/6.14; 435/7.1; 435/7.92

(58) Field of Classification Search
USPC ............................. 435/4, 6.12, 7.1, 7.23, 7.92
See application file for complete search history.

(56) References Cited

U.S. PATENT DOCUMENTS

| | | | |
|---|---|---|---|
| 5,118,801 | A | 6/1992 | Lizardi et al. |
| 5,210,015 | A | 5/1993 | Gelfand et al. |
| 5,312,728 | A | 5/1994 | Lizardi et al. |
| 5,538,848 | A | 7/1996 | Livak et al. |
| 5,763,570 | A | 6/1998 | Kauvar et al. |
| 5,767,086 | A | 6/1998 | Kauvar et al. |
| 5,866,336 | A | 2/1999 | Nazarenko et al. |
| 5,955,432 | A | 9/1999 | Kauvar et al. |
| 5,968,737 | A | 10/1999 | Ali-Osman et al. |
| 6,117,635 | A | 9/2000 | Nazarenko et al. |
| 2005/0004038 | A1 | 1/2005 | Lyon et al. |

OTHER PUBLICATIONS

Tockman et al (Cancer Res., 1992, 52:2711s-2718s).*
Pritzker (Clinical Chemistry, 2002, 48:1147-1150).*
Luo et al. (Oncogene, 2009, 28:4126-4132).*
Abravaya, K., et al., Detection of point mutations with a modified ligase chain reaction (Gap-LCR), Nucleic Acids Reasearch, vol. 23, No. 4, pp. 675-682, (1995).
Andersen, P. K., and Gill, R. D., Cox's Regression Model for Counting Processes: A Large Sample Study, Ann Stat. vol. 10, No. 4, pp. 1100-1120 (1982).
Brummelkamp et al., A System for Stable Expression of Short Interfering RNAs in Mammalian Cells, Science, vol. 296, pp. 550-553 (2002).
Camp, R. L., et al., A Decade of Tissue Microarrays: Progress in the Discovery and Validation of Cancer Biomarkers, J Clin Oncol, vol. 26, No. 34, pp. 5630-5637 (2008).
Comstock, K. E., et al., A Comparison of the Enzymatic and Physiochemical Properties of Human Glutathione Transferase M4-4 and Three Other Human Mu Class Enzymes, Arch Biochem Biophys, vol. 311, No. 2, pp. 487-495 (1994).
Comstock, K. E., et al., Isolation and Analysis of the Gene and cDNA for a Human Mu Class Glutathione S-Transferase, GSTM4, J Biol Chem, vol. 268, No. 23, pp. 16958-16965 (1993).
Delattre, O., et al., Gene fusion with an ETS DNA-binding domain caused by chromosome translocation in human tumours, Nature, vol. 359, pp. 162-165 (1992).
Flatgaard et al., Isozyme specificity of novel glutathione-S-transferase inhibitors, Cancer Chemother. Pharmacol. 33:63-70 (1993).
Gangwal, K. and Lessnick, S. L., Microsatellites are EWS/FLI response elements, Cell Cycle, 7:20, 3127-3132 (2008).
Gangwal, K., et al., Microsatellites as EWS/FLI response elements in Ewing's sarcoma, Proc Natl Acad Sci USA, vol. 105, No. 29, pp. 10149-10154 (2008).
Grambsch, P. M., and Therneau, T. M., Proportional hazards tests and diagnostics based on weighted residuals, Biometrika, 81, 3, pp. 515-526 (1994).
Hafner et al., Isothermal Amplification and Multimerization of DNA by Bst DNA Polymerase, Biotechniques 2001, vol. 30, No. 4, pp. 852-854, 856, 858, 860, 862, 864, 866-867.
Kievits, T., et al., NASBA™ isothermal enzymatic in vitro nucleic acid amplification optimized for the diagnosis of HIV-1 infection, J Virological Methods, 35, pp. 273-286, (1991).
Kinsey, M., et al., NROB1 Is Required for the Oncogenic Phenotype Mediated by EWS/FLI in Ewing's Sarcoma, Mol Cancer Res, vol. 4, No. 11, pp. 851-859 (2006).
Lessnick, S. L., et al., The Ewing's sarcoma oncoprotein EWS/FLI induces a p53-dependent growth arrest in primary human fibroblasts, Cancer Cell, vol. 1, pp. 393-401 (2002).
Livak et al., Oligonucleotides with fluorescent dyes at opposite ends provide a quenched probe system useful for detecting PCR product and nucleic acid hybridization, Genome Res: PCR Methods and Applns., 4, pp. 357-362 (1995).
Lyttle et al., Isozyme-Specific Glutathione-S-Transferase Inhibitors: Design and Synthesis, J. Med. Chem. 37:189-194 (1994).
Maniatis et al., Isolation of Bacteriophage and Plasmid DNA, Molecular Cloning, A Laboratory Manual, Cold Spring Harbor Laboratory, pp. 75-85 (1982).
May, W. A., et al., Ewing sarcoma 11;22 translocation produces a chimeric transcription factor that requires the DNA-binding domain encoded by FLI1 for transformation, Proc Natl Aced Sci USA, vol. 90, pp. 5752-5756 (1993).

(Continued)

Primary Examiner — Stephen Rawlings
Assistant Examiner — Yan Xiao
(74) Attorney, Agent, or Firm — Michael Best & Friedrich LLP

(57) ABSTRACT

Disclosed herein are diagnostic and prognostic methods for determining drug sensitivity and resistance in Ewing's sarcoma patients. Treatments for drug-resistant Ewing's sarcoma are also disclosed. The assays involve the detection of GSTM4 gene expression alone or in combination with other clinical factors. The tests are suitable for diagnosing and monitoring treatment of patients having or suspected of having Ewing's sarcoma. The disclosure also relates to inhibitors of GSTM4 for the treatment of Ewing's sarcoma, including drug-resistant forms thereof.

12 Claims, 6 Drawing Sheets

(56) References Cited

OTHER PUBLICATIONS

May, W. A., et al., The Ewing's Sarcoma EWS/FLI-1 Fusion Gene Encodes a More Potent Transcriptional Activator and Is a More Powerful Transforming Gene than FLI-1, Mol Cell Bio, vol. 13, No. 12, pp. 7393-7398 (1993).

Miyagishi and Taira, U6 promoter-driven siRNAs with four uridine 3' overhangs efficiently suppress targeted gene expression in mammalian cells, Nature Biotechnol., vol. 19, pp. 497-500 (2002).

Morgan et al., Isozyme-specific glutathione S-transferase inhibitors potentiate drug sensitivity in cultured human tumor cell lines, Cancer Chemother. Pharmacol., 37, pp. 363-370 (1996).

Nakamura, et al., Enzyme Immunoassays: Heterogeneous and Homogeneous Systems, Handbook of Experimental Immunology, vol. 1: Immunochemistry, 27.1-27.20 (1986).

Nazarenko et al., A closed tube format for amplification and detection of DNA based on energy transfer, Nucl. Acids Res., vol. 25:, No. 12, pp. 2516-2521 (1997).

Paul et al., Effective expression of small interfering RNA in human cells, Nature Biotechnol., vol. 20, pp. 505-508 (2002).

Peck et al., A method for high-throughput gene expression signature analysis, Genome Biol., 7(7):R61.1-R61.6 (2006).

Prieur, A., et al., EWS/FLI-1 Silencing and Gene Profiling of Ewing Cells Reveal Downstream Oncogenic Pathways and a Crucial Role for Repression of Insulin-Like Growth Factor Binding Protein 3, Mol Cell Bio, vol. 24, No. 16, pp. 7275-7283 (2004).

Rashtchian, A., Amplification of RNA, Genome Res: PCR Methods and Applns., 4:S83-S91, (1994).

Saiki, R.K., "Amplification of Genomic DNA", *PCR Protocols: A Guide to Methods and Applications* (eds M.A. Innis. D.H. Gelfand, J.J. Sninsky and T.J. White), (1990) pp. 13-20.

Smith, R., et al., Expression profiling of EWS/FLI identifies NKX2.2 as a critical target gene in Ewing's sarcoma, Cancer Cell, 9, pp. 405-416 (2006).

Sui et al., A DNA vector-based RNAi technology to suppress gene expression in mammalian cells, PNAS, vol. 99, No. 8, pp. 5515-5520 (2002).

Tyagi et al., Molecular Beacons: Probes that Fluoresce upon Hybridization, Nature Biotechnology, vol. 14, pp. 303-308 (1996).

Urdea, M.S., et al., Direct and quantitative detection of HIV-1 RNA in human plasma with a branched DNA signal amplification assay, AIDS, 7 (suppl 2): pp. S11-S14, (1993).

Wharam et al., Specific detection of DNA and RNA targets using a novel isothermal nucleic acid amplification assay based on the formation of a three-way junction structure, Nucleic Acids Res., 2001, vol. 29, No. 11, E54-E54, pp. 1-8.

Whelen et al., Direct Genotypic Detection of *Mycobacterium tuberculois* Rifampin Resistance in Clinical Specimens by Using Single-Tube Heminested PCR, J of Clin Micro, vol. 33, No. 3, pp. 556-561 (1995).

\* cited by examiner

DIAGNOSIS AND TREATMENT OF DRUG-RESISTANT EWING'S SARCOMA

TECHNICAL FIELD

The present disclosure relates generally to the diagnosis, prognosis, treatment, and management of disease, including cancer. In particular, the present technology relates to methods for detecting gene expression alterations associated with cancer and drug resistance. The present disclosure also relates to the treatment of cancer, including drug-resistant Ewing's sarcoma.

BACKGROUND

The following discussion of the background is merely provided to aid the reader in understanding the present disclosure and is not admitted to describe or constitute prior art.

Ewing's sarcoma is an aggressive and highly metastatic malignancy. It arises in and around the bones of the extremities and central skeleton, but may also arise in the soft tissues. Ewing's sarcoma primarily affects children and young adults, predominantly those of European descent, with the highest rates of development occurring in white male adolescents.

Cells of Ewing's sarcoma appear as small, round, undifferentiated blue cells, and thus belongs to a class of tumors with a similar histologic appearance which includes rhabdomyosarcoma, neuroblastoma, and lymphoma. However, the cellular origin of Ewing's sarcoma is unknown. Most cases of Ewing's sarcoma emanate via a recurrent chromosomal translocation that encodes for the EWS/FLI fusion protein. See Delattre, O., et al., *Nature*, 359, 162-165 (1992). The FLI portion contains an ETS family DNA-binding domain while the EWS portion functions as a strong transcriptional activation domain. Accordingly, EWS/FLI is an aberrant transcription factor that dysregulates genes involved in tumor development. See May, W. A., et al., *Proc Natl Acad Sci USA*, 90, 5752-5756 (1993a); May, W. A., et al., *Mol Cell Biol*, 13, 7393-7398 (1993b). A variety of studies have identified a large number of EWS/FLI-regulated genes. See, e.g., Prieur, A., et al., *Mol Cell Biol*, 24, 7275-7283 (2004). However, specific genes involved in the proliferation of Ewing's sarcoma oncogenesis have yet to be elucidated.

Glutathione S-transferases ("GSTs") are detoxification enzymes which inactivate a variety of endogenous and exogenous reactive compounds by conjugation to glutathione. At present, eight distinct classes (alpha, kappa, mu, omega, sigma, theta, pi, and zeta) of soluble and six membrane-bound GSTs have been identified. GSTM4 belongs to the mu class of soluble forms. See Comstock, K. E., et al., *J Biol Chem*, 268, 16958-16965 (1993); Comstock, K. E., et al., *Arch Biochem Biophys*, 311, 487-495 (1994).

SUMMARY

In one aspect, the present disclosure generally describes a method for determining a diagnosis or prognosis of Ewing's sarcoma in a subject, the method comprising: detecting a level of GSTM4 expression in a test sample from the subject, wherein a difference in the level of GSTM4 expression in the subject compared to a reference level is an indication of the subject's sensitivity or the subject's resistance to a chemotherapeutic agent, a GST-inhibitor, or GST-activated prodrug.

In one embodiment, an increase in the level of GSTM4 expression compared to the reference level indicates the subject's resistance to the chemotherapeutic agent. In one embodiment, an increase in the level of GSTM4 expression compared to the reference level indicates the subject's sensitivity to the GST-inhibitor or GST-activated prodrug. In one embodiment, the increase in the level of GSTM4 expression compared to the reference level indicates that the subject has a decreased overall survival compared to individuals that do not have the increase in the level of GSTM4 expression. In one embodiment, the sensitivity or the resistance indicates that the subject is a candidate for treatment with a GSTM4 inhibitor or a chemotherapeutic agent.

In one embodiment, the reference level is the level of GSTM4 expression in a comparable sample from one or more healthy individuals. In one embodiment, the reference level is the level of GSTM4 expression in a comparable sample from one or more individuals afflicted with Ewing's sarcoma.

In one embodiment, the chemotherapeutic agent selected from the group consisting of etoposide, fenretinide, vincristin, doxorubicin, cyclophosphamide, ifosfamide, topotecan, irinotecan, and temozolomide.

In one embodiment, the GST-inhibitor is a GSTM inhibitor. In one embodiment, the GSTM inhibitor is a GSTM4 inhibitor. In one embodiment, the GST-inhibitor is selected from the group consisting of NBDHEX, GST Inhibitor-1 (Cibacron Blue F3G-A); GST Inhibitor-2 (Ethacrynic acid); and 4-Aryl-1,3,2-oxathiazolylium-5-olate (OZO). In one embodiment, the GST-activated prodrug is JS-K. In one embodiment, the GST-inhibitor is a RNAi inhibitor. In one embodiment, the RNAi inhibitor is capable of selectively decreasing the GSTM4 expression.

In one embodiment, the detecting comprises amplifying a fragment of the GSTM4 mRNA. In one embodiment, the amplifying is by polymerase chain reaction (PCR) or RT-PCR. In one embodiment, the amplifying employs a detectably-labeled primer or probe.

In one embodiment, the detecting comprises measuring the presence, absence, or amount of a GSTM4 protein in the sample. In one embodiment, the measuring uses an antibody that specifically binds to the GSTM4 protein. In one embodiment, the measuring is by an ELISA assay, a Western blot assay, or an immunohistochemical assay.

In one embodiment, the sample is a biopsy sample. In one embodiment, the subject is a human patient having or suspected of having Ewing's sarcoma.

In one embodiment, the method includes (a) contacting a sample from a subject with one or more primers specific for GTSM4; (c) amplifying GTSM4 mRNA in the sample to form an amplification product; and (d) determining the subject's sensitivity or the subject's resistance to a chemotherapeutic agent, a GST-inhibitor, or GST-activated prodrug in the subject where the level of amplification product in the sample is greater than a reference level.

In one embodiment, the method includes (a) contacting a sample from a subject with one or more antibodies specific for GTSM4 to form a complex between the one or more antibodies and GTSM4 protein present in the sample; (b) measuring complexes formed to determine an amount of total GTSM level in the sample; and (c) determining the subject's sensitivity or the subject's resistance to a chemotherapeutic agent, a GST-inhibitor, or GST-activated prodrug in the subject where the total GTSM4 level in the sample is greater than a reference level.

In another aspect, the present disclosure generally provides a method for treating Ewing's sarcoma in a patient in need thereof, the method comprising: (a) administering an effective amount of a GST-inhibitor or a GST-activated prodrug to the subject; or (b) simultaneously, sequentially or separately administering to the subject an effective amount of the GST-inhibitor or GST-activated prodrug and an effective amount of a chemotherapeutic agent, wherein the GST-inhibitor improves the subject's responsiveness to the chemotherapeutic agent.

In one embodiment, the chemotherapeutic agent is etoposide, fenretinide, vincristin, doxorubicin, cyclophosphamide, ifosfamide, topotecan, irinotecan, temozolomide, or a combination thereof. In one embodiment, the effective amount of the etoposide is between 0.1 and 30 mg/kg of body weight of the subject. In one embodiment, the effective amount of the fenretinide is between 0.1 and 30 mg/kg of body weight of the subject.

DETAILED DESCRIPTION

Figure 1:
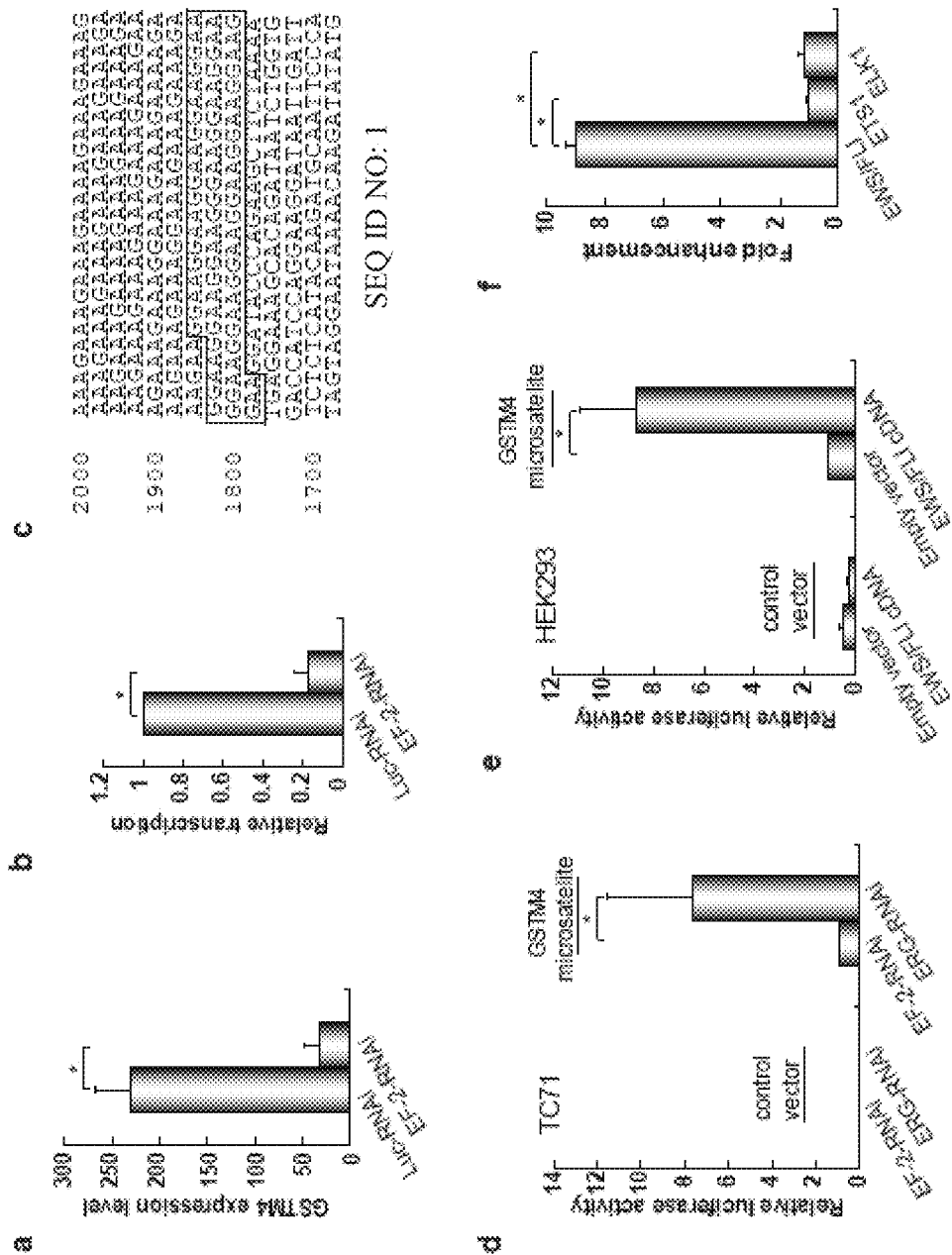
FIG. 1a is a graph showing decreased GSTM4 expression when an EF-2-RNAi construct is transfected into cells.
FIG. 1b is a graph representing the quantitative RT-PCR results for GSTM4 RNA levels from RNAi transfected A673 Ewing's sarcoma cells.
FIG. 1c is the partial sequence of the GSTM4 promoter with GGAA microsatellite regions indicated in the boxed region.
FIGS. 1d to 1e are graphs representing luciferase assay results using a vector containing the GSTM4 GGAA-microsatellite region.
FIG. 1f is a graph representing the results from chromatin immunoprecipitation assays employing anti-FLI, anti-ETS1, or anti-ELK1 antibodies. The fold enrichment of the GGAA-microsatellite-containing region is shown.

The present disclosure relates to the diagnosis, prognosis, and treatment of Ewing's sarcoma family tumors (ESFT). ESFT or Ewing's sarcoma are highly aggressive cancers in which drug-resistant disease remains a significant clinical problem. Accordingly, the present disclosure relates to the diagnosis of Ewing's sarcoma oncogenesis, including the prognostic determination thereof. The present disclosure further includes methods for determining and predicting Ewing's sarcoma oncogenic phenotypes, such as drug-resistant Ewing's sarcoma. Methods are described for the quantification of mRNA or protein levels of a GST biomarker in order to assist an oncologist in the determination of a specific Ewing's sarcoma phenotype, i.e., drug-resistant Ewing's sarcoma.

In one aspect, the methods provide for a prognostic determination of drug-resistant Ewing's sarcoma based on elevated expression levels of GSTM4. In one embodiment, a determination of drug-resistant Ewing's sarcoma indicates resistance to chemotherapeutic agents. In one embodiment, a determination of drug-resistant Ewing's sarcoma indicates sensitivity to GST-inhibitors or GST-activated prodrugs. In one embodiment, a determination of drug-resistant Ewing's sarcoma indicates the overall survival for a Ewing's sarcoma patient is decreased.

The present disclosure also includes methods for determining and treating Ewing's sarcoma oncogenesis, including the identification and treatment of drug-resistant Ewing's sarcoma. Methods for treating Ewing's sarcoma in a patient include administering effective amounts of GST-inhibitors, e.g. a GSTM4 inhibitor or GST-activated prodrugs. The methods of the present disclosure provide a treatment regime that may be selected based upon the diagnosis or prognosis of Ewing's sarcoma. In one embodiment, a treatment regime is selected based upon elevated expression levels of GSTM4.

The methods further include individual or combination therapies employing GST-inhibitors or GST-activated prodrugs in the presence or absence of chemotherapeutic agents. Individual or combination therapy is beneficial when it is determined prior to treatment that a GST-inhibitor will increase a subject's sensitivity to chemotherapeutic agents.

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a nucleic acid" includes a combination of two or more nucleic acids, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

As used herein, the "administration" of an agent or drug to a subject or subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

As used herein, the terms "amplification" or "amplify" mean one or more methods known in the art for copying a target nucleic acid, e.g., GSTM4 mRNA, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in *PCR Protocols*, Innis et al., Eds., Academic Press, San Diego, Calif. 1990, pp. 13-20; Wharam et al., *Nucleic Acids Res.*, 2001, 29(11):E54-E54; Hafner et al., *Biotechniques* 2001, 30(4):852-6, 858, 860; Zhong et al., *Biotechniques*, 2001, 30(4):852-6, 858, 860.

As used herein the term "antibody" refers to an immunoglobulin and any antigen-binding portion of an immunoglobulin, e.g., IgG, IgD, IgA, IgM and IgE, or a polypeptide that contains an antigen binding site, which specifically binds or "immunoreacts with" an antigen. Antibodies can comprise at least one heavy (H) chain and at least one light (L) chain inter-connected by at least one disulfide bond. The term "$V_H$" refers to a heavy chain variable region of an antibody. The term "$V_L$" refers to a light chain variable region of an antibody. In exemplary embodiments, the term "antibody" specifically covers monoclonal and polyclonal antibodies. A "polyclonal antibody" refers to an antibody which has been derived from the sera of animals immunized with an antigen or antigens. A "monoclonal antibody" refers to an antibody produced by a single clone of hybridoma cells.

The term "clinical factors" as used herein, refers to any data that a medical practitioner may consider in determining a diagnosis or prognosis of disease. Such factors include, but are not limited to, the patient's medical history, a physical examination of the patient, complete blood count, etc.

As used herein a "confidence interval" or "CI" refers to a measure of the precision of an estimated or calculated value. The interval represents the range of values, consistent with the data that is believed to encompass the "true" value with high probability (usually 95%). The confidence interval is expressed in the same units as the estimate or calculated value. Wider intervals indicate lower precision; narrow intervals indicate greater precision. Suitable confidence intervals of the present disclosure included, but are not limited to 90%, 95%, 97.5%, 98%, 99%, 99.5%, 99.9% and 99.99%.

The term "comparable" or "corresponding" in the context of comparing two or more samples, means that the same type of sample, e.g., tissue is used in the comparison. For example, an expression level of GSTM4 mRNA or protein in a tissue or biopsy sample can be compared to an expression level of GSTM4 in another whole blood sample. In some embodiments, comparable samples may be obtained from the same individual at different times. In other embodiments, comparable samples may be obtained from different individuals, e.g., a patient and a healthy individual. In general, comparable samples are normalized by a common factor. For example, body fluid samples are typically normalized by volume body fluid and cell-containing samples are normalized by protein content or cell count.

The terms "determining," "measuring," "assessing," and "assaying" are used interchangeably and include both quantitative and qualitative determinations. These terms refer to any form of measurement, and include determining if a characteristic, trait, or feature is present or not. Assessing may be relative or absolute. "Assessing the presence of" includes determining the amount of something present, as well as determining whether it is present or absent.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease, i.e. there may be differential diagnoses that can be inferred from a diagnostic factor or symptom. Likewise, there may be instances where a factor or symptom that is indicative of a particular disease is present in an individual that does not have the particular disease. The term "diagnosis" also encompasses determining the therapeutic effect of a drug therapy, or predicting the pattern of response to a drug therapy. The diagnostic methods may be used independently, or in combination with other diagnosing and/or staging methods known in the medical arts for a particular disease or disorder, e.g., Ewing's sarcoma or ESFT.

As used herein, the phrase "difference of the level" refers to differences in the quantity of a particular marker, such as a biomarker protein or nucleic acid, in a sample as compared to a control or reference level. For example, the quantity of particular protein or nucleic acid may be present at an elevated amount or at a decreased amount in samples of patients with a disease compared to a reference level. In one embodiment, a "difference of a level" may be a difference between the level of biomarker present in a sample as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more. In one embodiment, a "difference of a level" may be a statistically significant difference between the level of the biomarker present in a sample as compared to a control. For example, a difference may be statistically significant if the measured level of the biomarker falls outside of about 1.0 standard deviations, about 1.5 standard deviations, about 2.0 standard deviations, or about 2.5 stand deviations of the mean of any control or reference group.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

The term "elevated levels" or "higher levels" as used herein refers to levels of a biomarker protein or nucleic acid that are higher than what would normally be observed in a comparable sample from control or normal subjects, i.e., a reference value. In some embodiments, "control levels", i.e., normal levels, refer to a range of biomarker protein or nucleic acid levels that would normally be expected to be observed in a sample from a mammal that does not have a disease. A control level may be used as a reference level for comparative purposes. "Elevated levels" refer to biomarker protein or nucleic acid levels that are above the range of control levels. The ranges accepted as "elevated levels" or "control levels" are dependent on a number of factors. For example, one laboratory may routinely determine the level of biomarker protein or nucleic acid in a sample that are different than the level obtained for the same sample by another laboratory. Also, different assay methods may achieve different value ranges. Value ranges may also differ in various sample types, for example, different body fluids or by different treatments of the sample. One of ordinary skill in the art is capable of considering the relevant factors and establishing appropriate reference ranges for "control values" and "elevated values" of the present disclosure. For example, a series of samples from control subjects and subjects diagnosed with cancer can be used to establish ranges that are "normal" or "control" levels and ranges that are "elevated" or "higher" than the control range.

Similarly, "reduced levels" or "lower levels" as used herein refer to levels of a biomarker protein or nucleic acid that are lower than what would normally be observed in a comparable sample from control or normal subjects, i.e., a reference value. In some embodiments, "control levels", i.e., normal levels, refer to a range of biomarker protein or nucleic acid levels that would be normally be expected to be observed in a mammal that does not have a disease and "reduced levels" refer to biomarker protein or nucleic acid levels that are below the range of control levels.

The term "enzyme linked immunosorbent assay" or "ELISA" as used herein refers to an antibody-based assay in which detection of the antigen of interest is accomplished via an enzymatic reaction producing a detectable signal. An ELISA can be run as a competitive or non-competitive format. ELISA also includes a 2-site or "sandwich" assay in which two antibodies to the antigen are used, one antibody to capture the antigen and one labeled with an enzyme or other detectable label to detect captured antibody-antigen complex. In a typical 2-site ELISA, the antigen has at least one epitope to which unlabeled antibody and an enzyme-linked antibody can bind with high affinity. An antigen can thus be affinity captured and detected using an enzyme-linked antibody. Typical enzymes of choice include alkaline phosphatase or horseradish peroxidase, both of which generate a detectable product when contacted by appropriate substrates.

As used herein, a "fragment" in the context of a nucleic acid refers to a sequence of nucleotide residues which are at least about 5 nucleotides, at least about 7 nucleotides, at least about 9 nucleotides, at least about 11, nucleotides, or at least about 17, nucleotides. A fragment is typically less than about 300 nucleotides, less than about 100 nucleotides, less than about 75 nucleotides less than about 50 nucleotides, or less than about 30 nucleotides. In certain embodiments, the fragments can be used in polymerase chain reaction (PCR), or various hybridization procedures to identify or amplify identical or related DNA molecules.

As used herein, the terms "gene expression" or "expression" refer to the process of converting genetic information encoded in a gene into RNA, e.g., mRNA, rRNA, tRNA, or snRNA, through transcription of the gene, i.e., via the enzymatic action of an RNA polymerase, and for protein encoding genes, into protein through translation of mRNA. Gene expression can be regulated at many stages in the process. "Up-regulation" or "activation" refers to regulation that increases the production of gene expression products, i.e., RNA or protein, while "down-regulation" or "repression" or "knock-down" refers to regulation that decrease production. Molecules, e.g., transcription factors that are involved in up-regulation or down-regulation are often called "activators" and "repressors," respectively.

As used herein, the term "introduce" refers to the incorporation of a nucleic acid into a eukaryotic or prokaryotic cell where the nucleic acid may be incorporated into the genome of the cell, e.g., chromosome, plasmid, plastid, or mitochondrial DNA, converted into an autonomous replicon, or transiently expressed, e.g., infected mRNA. The term includes such nucleic acid introduction means as transfection, transformation, and transduction.

As used herein, "microarray" or "array" or "tissue microarray" refers to an arrangement of a collection of nucleic acids, e.g., nucleotide sequences in a centralized location. Arrays can be on a solid substrate, such as a glass slide, or on a semi-solid substrate, such as nitrocellulose membrane. The nucleotide sequences can be DNA, RNA, or any combination or permutations thereof. The nucleotide sequences can also be partial sequences or fragments from a gene, primers, whole gene sequences, non-coding sequences, coding sequences, published sequences, known sequences, or novel sequences. Tissue microarrays are well known in the art and can be performed as described. See e.g., Camp, R. L., et al., *J Clin Oncol*, 26, 5630-5637 (2008).

As used herein, "nucleic acid" refers broadly to segments of a chromosome, segments or portions of DNA, cDNA, and/or RNA. Nucleic acid may be derived or obtained from an originally isolated nucleic acid sample from any source, e.g., isolated from, purified from, amplified from, cloned from, or reverse transcribed from sample DNA or RNA.

As used herein, the term "oligonucleotide" refers to a short polymer composed of deoxyribonucleotides, ribonucleotides or any combination thereof. Oligonucleotides are generally between about 10 and about 100 nucleotides in length. Oligonucleotides are typically 15 to 70 nucleotides long, with 20 to 26 nucleotides being the most common. An oligonucleotide may be used as a primer or as a probe. An oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, or at least 95% sequence identity.

As used herein, the term "overall survival" or "OS" is used to refer to time in years from treatment to death from any cause. The calculation of this measure may vary depending on the definition of events to be either censored or not considered.

As used herein, the term "p-value" refers to a measure of probability that a difference between groups happened by chance. For example, a difference between two groups having a p-value of 0.01 (or p=0.01) means that there is a 1 in 100 chance the result occurred by chance. Suitable p-values include, but are not limited to, 0.1, 0.05, 0.025, 0.02, 0.01, 0.005, 0.001, and 0.0001.

As used herein, the terms "polypeptide," "peptide," and "protein" are used interchangeably to refer to a polymer of amino acid residues. The terms apply to amino acid polymers in which one or more amino acid residues is an artificial chemical analog of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms polypeptide, peptide, and protein are also inclusive of modifications including, but not limited to, glycosylation, lipid attachment, sulfation, carboxylation, hydroxylation, ADP-ribosylation, and addition of other complex polysaccharides.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, a positive prognosis is one where a patient has a 50% probability of being cured of a particular cancer, e.g., Ewing's sarcoma, after treatment, while the average patient with the same cancer has only a 25% probability of being cured.

As used herein, the term "reference level" refers to a level of a substance which may be of interest for comparative purposes. In one embodiment, a reference level may be the expression level of a protein or nucleic acid expressed as an average of the level of the expression level of a protein or nucleic acid from samples taken from a control population of healthy (disease-free) subjects. In another embodiment, the reference level may be the level in the same subject at a different time, e.g., before the present assay, such as the level determined prior to the subject developing the disease or prior to initiating therapy. In general, samples are normalized by a common factor. For example, body fluid samples are normalized by volume body fluid and cell-containing samples are normalized by protein content or cell count.

As used herein, the term "RNA interference" or "RNAi" refers to the process of sequence-specific post-transcriptional gene silencing mediated by short interfering nucleic acids (siRNAs). The term "RNAi construct" refers to siRNAs as well as DNA and RNA vectors that encode siRNAs when transcribed within a cell.

Similarly, as used herein, the term "siRNA" refers to short interfering nucleic acid. The term is meant to be equivalent to other terms used to describe nucleic acid molecules that are capable of mediating sequence specific RNA interference, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others.

As used herein, the term "sample" or "test sample" refers to any liquid or solid material containing nucleic acids or proteins. In suitable embodiments, a test sample is obtained from a biological source, i.e., a "biological sample", such as cells in culture or a tissue sample from an animal, most preferably, a human. In an exemplary embodiment, the sample is a tumor sample.

As used herein, the term "subject" refers to a mammal, such as a human, but can also be another animal such as a domestic animal, e.g., a dog, cat, or the like, a farm animal, e.g., a cow, a sheep, a pig, a horse, or the like, or a laboratory animal, e.g., a monkey, a rat, a mouse, a rabbit, a guinea pig, or the like. The term "patient" refers to a "subject" who is, or is suspected to be, afflicted with Ewing's sarcoma.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, "target nucleic acid" refers to segments of a chromosome, a complete gene with or without intergenic sequence, segments or portions a gene with or without intergenic sequence, or sequence of nucleic acids to which probes or primers are designed. Target nucleic acids may be derived from genomic DNA, cDNA, or RNA. As used herein, target nucleic acid may be native DNA or a PCR-amplified product. In one embodiment, the target nucleic acid is a fragment of a chromosome to be analyzed for methylation, e.g., a promoter region of a gene. In some embodiments, the target nucleic acid is a segment of the GSTM4 mRNA.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a disorder if, after receiving a therapeutic agent according to the methods of the present disclosure, the subject shows observable and/or measurable reduction in or absence of one or more signs and symptoms of a particular disease or condition.

Overview

Disclosed herein are methods for detecting the presence or absence of Ewing's sarcoma or a particular Ewing's sarcoma phenotype, i.e., drug-resistant Ewing's sarcoma. The methods described herein are designed to detect Ewing's sarcoma, if present, in a sample from a subject. The samples consist of, but are not limited to, sputum, blood (or a fraction of blood such as plasma, serum, or particular cell fractions), lymph, mucus, tears, saliva, urine, semen, ascites fluid, whole blood, and biopsy samples of body tissue. In one embodiment, the sample is tissue from a suspected Ewing's sarcoma tumor.

At least in part, the methods of the present disclosure are based on results of assays indicating that a patient is afflicted with Ewing's sarcoma. In one embodiment, the methods indicate that the patient is afflicted with a drug-resistant form of Ewing's sarcoma. In one embodiment, it can be determined that a patient has drug-resistant Ewing's sarcoma when results indicate elevated levels of a biomarker, i.e., GSTM4 mRNA or a GSTM4 protein, in a sample. In one embodiment, elevated levels of GSTM4 mRNA or a GSTM4 protein are prognostic for drug-resistant Ewing's sarcoma when compared to a reference level. In one embodiment, drug-resistant Ewing's sarcoma is prognostic for decreased overall survival in a Ewing's sarcoma patient.

The present inventors discovered that over-expression of GST promotes drug resistance and cancer cell proliferation in patient's with Ewing's sarcoma. Without wishing to be limited by theory, overexpression of GSTM4, a member of the mu class of soluble GST proteins, may provide the mechanism for the drug-resistance phenotypes of Ewing's sarcoma in patients. Moreover, compared to other GST and GST mu proteins, GSTM4 has a high level of amino acid sequence identity, yet GSTM4 has distinct physiochemical properties and tissue distributions. See Comstock et al., (1993); and Comstock et al., (1994). However, GSTM4 does not show comparable activity with standard GST substrates, and a specific GSTM4 substrate has yet to be identified. Accordingly, the physiological properties of GSTM4, and its expression profile in Ewing's sarcoma patients, make GSTM4 a suitable biomarker for diagnosis and prognosis of disease, i.e., Ewing's sarcoma.

In one aspect, the present methods provide for the detection, measuring, and comparison of a pattern of GSTM4 protein or mRNA expression in a sample. In one embodiment, the present methods provide for the detection of Ewing's sarcoma or drug-resistant Ewing's sarcoma in a sample via comparison to control samples. In one embodiment, drug-resistant Ewing's sarcoma is indicated by elevated mRNA or protein expression levels relative to expression levels seen in patients that do not have drug-resistant Ewing's sarcoma. Additional diagnostic markers may be combined with a GSTM4 expression profile to construct models for predicting the presence or absence or stage of a disease, i.e., Ewing's sarcoma. For example, relevant clinical factors for diagnosing Ewing's sarcoma, include, but are not limited to, the subject's medical history, a physical examination, complete blood count, and other markers. Moreover, biomarkers relevant to Ewing's sarcoma may be combined with a patient's GSTM4 expression profile for diagnosis or prognosis, e.g., CD99 mRNA or protein expression levels.

In one aspect, a determination that the patient has drug-resistant Ewing's sarcoma is an indicator for decreased overall survival, i.e. a shortened period of time from treatment to death from any cause. In one embodiment, treatment includes administering a GST-inhibitor. In one embodiment the GST-inhibitor inhibits GSTM4. In one embodiment, the GST-inhibitor is 6-(7-nitro-2,1,3-benzoxadiazol-4-ylthio) hexanol ("NBDHEX"). In one embodiment, the GST-inhibitor is an RNAi inhibitor that specifically reduces GSTM4 expression. In one embodiment, treatment includes administering a GST-activated prodrug. In one embodiment, the GST-activated prodrug is a Nitric oxide (NO) prodrug of the diazeniumdiolate class. In one embodiment, the nitric acid prodrug is $O^2$-(2,4-Dinitrophenyl)1-[(4-Ethoxycarbonyl)piperazin-1-yl]diazen-1-ium-1,2-diolate ("JS-K"). The present disclosure also provides for combination chemotherapy. In one embodiment, the treatment includes administering a GST-inhibitor and a chemotherapeutic agent. In one embodiment, the chemotherapeutic agent is etoposide or fenretinide.

Methods for Nucleic Acid Detection

The nucleic acid to be amplified may be from a biological sample such as a tissue sample and the like. Various methods of extraction are suitable for isolating the DNA or RNA. Suitable methods include phenol and chloroform extraction. See Maniatis et al., *Molecular Cloning, A Laboratory Manual*, 2d, Cold Spring Harbor Laboratory Press, pp. 16-54 (1989). Numerous commercial kits also yield suitable DNA and RNA including, but not limited to, QIAamp™ mini blood kit, Agencourt Genfind™, Roche Cobas® Roche MagNA Pure® or phenol: chloroform extraction using Eppendorf Phase Lock Gels®, and the NucliSens extraction kit (Biomerieux, Marcy l'Etoile, France).

Nucleic acid extracted from cells or tissues can be amplified using nucleic acid amplification techniques well known in the art. By way of example, but not by way of limitation, these techniques can include polymerase chain reaction (PCR), reverse transcriptase polymerase chain reaction (RT-PCR), nested PCR, ligase chain reaction. See Abravaya, K., et al., *Nucleic Acids Research*, 23:675-682, (1995), branched DNA signal amplification, Urdea, M. S., et al., *AIDS*, 7 (suppl 2):S11-S14, (1993), amplifiable RNA reporters, Q-beta replication, transcription-based amplification, boomerang DNA amplification, strand displacement activation, cycling probe technology, isothermal nucleic acid sequence based amplification (NASBA). See Kievits, T. et al., *J Virological Methods*, 35:273-286, (1991), Invader Technology, or other sequence replication assays or signal amplification assays may also be used. Some of these methods of amplification are described briefly below and are well-known in the art.

Some methods employ reverse transcription of RNA to cDNA. The method of reverse transcription and amplification may be performed by previously published or recommended procedures. Various reverse transcriptases may be used, including, but not limited to, MMLV RT, RNase H mutants of MMLV RT such as Superscript and Superscript II (Life Technologies, GIBCO BRL, Gaithersburg, Md.), AMV RT, and thermostable reverse transcriptase from *Thermus thermophilus*. For example, one method which may be used to convert RNA to cDNA is the protocol adapted from the Superscript II Preamplification system (Life Technologies, GIBCO BRL, Gaithersburg, Md.; catalog no. 18089-011), as described by Rashtchian, A., *PCR Methods Applic.*, 4:S83-S91, (1994).

In one embodiment, PCR is used to amplify a target sequence of interest, i.e., a GSTM4 sequence. PCR is a technique for making many copies of a specific template DNA sequence. The reaction consists of multiple amplification cycles and is initiated using a pair of primer sequences that hybridize to the 5' and 3' ends of the sequence to be copied. The amplification cycle includes an initial denaturation, and typically up to 50 cycles of annealing, strand elongation and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan et al., *J of Clin Micro*, 33(3):556-561 (1995). Briefly, a PCR reaction mixture includes two specific primers, dNTPs, approximately 0.25 U of Taq polymerase, and 1×PCR Buffer.

The skilled artisan is capable of designing and preparing primers that are appropriate for amplifying a target or marker sequence. The length of the amplification primers depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill. For example, the length of a short nucleic acid or oligonucleotide can relate to its hybridization specificity or selectivity. Exemplary primers for detecting GSTM4 mRNA may be designed based on the cDNA sequence available at GenBank Accession No. M96234. For example, primers may include: GSTM4.F: 5'-TCTGCCCTACTTGATTGATGG-3' (SEQ ID NO: 2); GSTM4.R: 5'-TGATTGGAGACGTCCATAGCC-3' (SEQ ID NO: 3).

In some embodiments, the amplification may include a labeled primer or probe, thereby allowing detection of the amplification products corresponding to that primer or probe. In one embodiment, the amplification may include a multiplicity of labeled primers or probes; such primers may be distinguishably labeled, allowing the simultaneous detection of multiple amplification products. In one embodiment, a primer or probe is labeled with a fluorogenic reporter dye that emits a detectable signal. While a suitable reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Edans, Eosin, Erythrosin, Fluorescein, 6-Fam, Tet, Joe, Hex, Oregon Green, Rhodamine, Rhodol Green, Tamra, Rox, and Texas Red.

In another embodiment, the detection reagent may be further labeled with a quencher dye such as Tamra, Dabcyl, or Black Hole Quencher® ("BHQ"), especially when the reagent is used as a self-quenching probe such as a TaqMan®, See U.S. Pat. Nos. 5,210,015 and 5,538,848, or Molecular Beacon probe, See U.S. Pat. Nos. 5,118,801 and 5,312,728, or other stemless or linear beacon probes. See Livak et al., *PCR Method Appl.*, 4:357-362 (1995); Tyagi et al, *Nature Biotechnology*, 14:303-308 (1996); Nazarenko et al., *Nucl. Acids Res.*, 25:2516-2521 (1997); and U.S. Pat. Nos. 5,866,336 and 6,117,635.

Nucleic acids may be amplified prior to detection or may be detected directly during an amplification step, i.e., "real-time" methods. In some embodiments, the target sequence is amplified using a labeled primer such that the resulting amplicon is detectably labeled. In some embodiments, the primer is fluorescently labeled. In some embodiments, the target sequence is amplified and the resulting amplicon is detected by electrophoresis.

In one embodiment, the level of gene expression can be determined by assessing the amount of GSTM4 mRNA in a test sample. Methods of measuring mRNA in samples are known in the art. To measure mRNA levels, the cells in the samples can be lysed and the levels of mRNA in the lysates or in RNA purified or semi-purified from lysates can be measured by any variety of methods familiar to those in the art. Such methods include, without limitation, hybridization assays using detectably labeled DNA or RNA probes, i.e., Northern blotting, or quantitative or semi-quantitative RT-PCR methodologies using appropriate oligonucleotide primers. Alternatively, quantitative or semi-quantitative in situ hybridization assays can be carried out using, for example, tissue sections, or unlysed cell suspensions, and detectably labeled, e.g., fluorescent, or enzyme-labeled, DNA or RNA probes. Additional methods for quantifying mRNA include RNA protection assay ("RPA"), cDNA and oligonucleotide microarrays, representation difference analysis ("RDA"), differential display, EST sequence analysis, serial analysis of gene expression ("SAGE"), and multiplex ligation-mediated amplification with the Luminex FlexMAP ("LMF"). See Peck et al., *Genome Biol.*, 7(7):R61 (2006).

Amplification may be also monitored using "real-time" methods. Real time PCR allows for the detection and quantitation of a nucleic acid target. Typically, this approach to quantitative PCR utilizes a fluorescent dye, which may be a double-strand specific dye, such as SYBR Green® I. Alternatively, other fluorescent dyes, e.g., FAM or HEX, may be conjugated to an oligonucleotide probe or a primer. Various instruments capable of performing real time PCR are known in the art and include, for example, ABI Prism® 7900 (Applied Biosystems) and LightCycler® systems (Roche). The fluorescent signal generated at each cycle of PCR is proportional to the amount of PCR product. A plot of fluorescence versus cycle number is used to describe the kinetics of amplification and a fluorescence threshold level is used to define a fractional cycle number related to initial template concentration. When amplification is performed and detected on an instrument capable of reading fluorescence during thermal cycling, the intended PCR product from non-specific PCR products can be differentiated using melting analysis. By measuring the change in fluorescence while gradually increasing the temperature of the reaction subsequent to amplification and signal generation it may be possible to determine the $T_m$ of the intended product(s) as well as that of the nonspecific product.

The methods may include amplifying multiple nucleic acids in sample, also known as "multiplex detection" or "multiplexing." As used herein, the term "multiplex PCR" refers to PCR, which involves adding more than one set of PCR primers to the reaction in order to detect and quantify multiple nucleic acids, including nucleic acids from one or more target gene markers. Furthermore, multiplexing with an internal control, e.g., 18s rRNA, GADPH, or β-actin) provides a control for the PCR without reaction.

In one embodiment, the methods include measuring the level of GSTM4 mRNA transcript. Microarrays are an array of distinct polynucleotides or oligonucleotides synthesized on a substrate, such as paper, nylon or other type of membrane, filter, chip, glass slide, or any other suitable solid support. In other embodiments, the microarray is composed of a large number of unique, single-stranded nucleic acid sequences, usually either synthetic antisense oligonucleotides or fragments of cDNAs, fixed to a solid support. Polynucleotides used in the microarray may be oligonucleotides or fragments that are specific to a gene or genes of interest, e.g., GSTM4.

In one embodiment, fluorescence-labeled single strand (or "first strand") cDNA probe is made from total or mRNA by first isolating RNA from the sample of cells to be tested for Ewing's sarcoma and cells of a control. Typically, the two cDNA samples are labeled with different fluorescent dyes, e.g. green Cy3 and red Cy5. The two labeled cDNA samples are mixed and hybridized to the microarray, and the slide is scanned. In the resulting image, the green Cy3 and red Cy5 signals are overlaid—yellow spots indicate equal intensity for the dyes. With the use of image analysis software, signal intensities are determined for each dye at each element of the array, and the logarithm of the ratio of Cy5 intensity to Cy3 intensity is calculated (center). Positive log(Cy5/Cy3) ratios indicate relative excess of the transcript in the Cy5-labeled sample, and negative log(Cy5/Cy3) ratios indicate relative excess of the transcript in the Cy3-labeled sample. Values near zero indicate equal abundance in the two samples. In one embodiment, tissue microarray analysis ("TMA"), is employed for GSTM4 mRNA detection when the sample is a tissue sample. See Camp, R. L., et al., *J Clin Oncol*, 26, 5630-5307 (2008).

Methods for Conducting Protein Assays

In one embodiment, the methods provide for detection of GSTM4 protein levels. The presence of GSTM4 can be measured by immunoassay, using antibodies specific for GSTM4 protein. Lack of antibody binding would indicate the absence of GSTM4 protein molecules and suggest that the subject does not have or is not susceptible to Ewing's sarcoma. An exemplary GSTM4 antibody is commercially available from Abcam (Ab-49484; Cambridge, Mass.).

GSTM4 antibodies may be obtained in a number of ways which will be readily apparent to those skilled in the art. The protein can be produced in a recombinant system using the nucleotide sequence of GSTM4 (GenBank Accession No. M96233). The recombinant protein can be injected into an animal as an immunogen to elicit polyclonal antibody production. The resultant polyclonal antisera may be used directly or may be purified by, for example, affinity absorption using recombinantly produced GSTM4 coupled to an insoluble support.

In one embodiment, GSTM4 proteins can be detected by immunohistochemistry, immunofluorescence, ELISPOT, ELISA, or RIA. The steps of various useful immunodetection methods have been described in the scientific literature, such as, e.g. Maggio et al., *Enzyme-Immunoassay*, (1987) and Nakamura, et al., *Enzyme Immunoassays: Heterogeneous and Homogeneous Systems, Handbook of Experimental Immunology. Vol. 1: Immunochemistry*, 27.1-27.20 (1986). Immunoassays are binding assays involving interactions between antibodies and antigen. Many types and formats of immunoassays are known and all are suitable for detecting the disclosed biomarker, i.e., GSTM4. Examples of immunoassays are enzyme linked immunosorbent assays ("ELISAs"), enzyme linked immunospot assay (ELISPOT), radioimmunoassays ("RIA"), radioimmune precipitation assays (RIPA), immunobead capture assays, Western blotting, dot blotting, gel-shift assays, Flow cytometry, immunohistochemistry, fluorescence microscopy, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, e.g., U.S. Pat. Nos. 3,817,837; 3,850,752; 3,939,350; 3,996,345; 4,277,437; 4,275,149 and 4,366,241.

In one embodiment, the level of GSTM4 protein or mRNA expression, in a sample, can be compared with levels observed in a control sample. A control may be any sample of cells where Ewing's sarcoma is absent. For example, a control sample may be non-cancerous cells, including, but not limited to normal human fibroblasts, human umbilical endothelial cells (HUVECs), or mesenchymal stem cells, which may be the cell of origin of Ewing's sarcoma. A control sample may further include any tumor cell type that is not Ewing's sarcoma including, for example, HEK293, HeLa, HCT116, MCF7, 501MEL, LNCaP, PC3, BT-20, SK-BR-3, and SK-OV-3. Also, any other pediatric tumor type where Ewing's sarcoma is absent would be an appropriate control sample. These could include HOS, OST, SAOS, MG-63, U2OS, RD, TTC442, CCL-136, HR, JR, RH28, RH30, Birch, CHLA 20, CHP 126, and CHLA 90. A control sample may also be cancerous cells derived from Ewing's sarcoma patients. For example, a control sample may be cancerous cells, including, but not limited to A673, TC71, EWS502, IARC-EW1, IARC-EW3, IARC-EW7, IARC-EW11, IARCEW12, IARC-EW14, IARC-EW15, IARC-EW16, IARCEW17, SK-N-MC, and SK-ES1.

Diagnosis of Disease States

In one aspect of the present disclosure, the information obtained from comparative GSTM4 expression analysis is used to diagnose Ewing's sarcoma. In one embodiment, GSTM4 expression is employed for determining the diagnosis of a subject. If GSTM4 is expressed at a higher level in the subject's sample compared to the level in a non-cancerous control sample then it is likely that the sample is from a Ewing's sarcoma patient, i.e., the subject is diagnosed as a Ewing's sarcoma patient. In one embodiment, an increase or decrease in GSTM4 expression levels may be used in conjunction with other clinical factors to diagnose Ewing's sarcoma. In one embodiment, GSTM4 expression is employed for determining whether a subject is a candidate for treatment. In one embodiment, if the subject is a patient with Ewing's sarcoma, then the patient is a candidate for treatment. In one embodiment, treatment includes chemotherapeutic agents, GST-inhibitors, or any combination thereof.

In one embodiment, the information obtained from comparative GSTM4 expression analysis is used to diagnose a drug-resistant form of Ewing's sarcoma. In one embodiment, GSTM4 expression is employed for determining the diagnosis or prognosis of a patient. If GSTM4 is expressed at a higher level in the patient's sample compared to the level of a Ewing's sarcoma control sample then it is likely that the sample is from a patient with drug-resistant Ewing's sarcoma. In one embodiment, an increase or decrease in GSTM4 expression levels may be used in conjunction with other clinical factors to diagnose drug-resistant Ewing's sarcoma. In one embodiment, GSTM4 gene expression is employed for determining whether a patient is a candidate for treatment. In one embodiment, if the patient has drug-resistant Ewing's sarcoma, then the patient is a candidate for treatment. In one embodiment, treatment includes chemotherapeutic agents, GST-inhibitors, or any combination thereof.

In one aspect, if the patient is diagnosed with drug-resistant Ewing's sarcoma then the patient has a decreased overall survival risk. Accordingly, the present disclosure also provides for prognostic overall survival determination of a patient based on GSTM4 levels in a sample. Thus, the present disclosure provides for determining the mortality risk of Ewing's sarcoma patients based at least partially on results of tests on a sample. In one embodiment, overall survival determination or mortality risk is based on GSTM4 expression levels in a sample. In one embodiment, overall survival determination or mortality risk is based on GSTM4 expression levels in a sample when compared to a control sample.

Compositions and Methods for Treatment of Ewing's Sarcoma

One aspect of the present disclosure identifies GSTM4 as a target for therapeutic intervention. Blocking or disrupting the expression of GSTM4 in cancerous cells would prevent or disrupt the ability of Ewing's sarcoma cells to propagate. Thus, the present disclosure provides for compositions and methods that are useful for modulating the expression of GSTM4 to treat Ewing's sarcoma. In one aspect, the present disclosure includes a composition comprising a therapeutic agent, i.e., a drug, and a pharmaceutically acceptable carrier.

In one embodiment the drug is a chemotherapeutic agent capable of killing cancerous cells. In one embodiment the drug is a topoisomerase inhibitor or a retinoid. In one embodiment the drug is etoposide or fenretinide. In one embodiment, the drug is present in an effective amount to reduce the expression of GSTM4 in cancerous cells. In one embodiment, the drug is NBDHEX, JS-K, or an RNAi construct. In one embodiment, the therapeutic agent is a combination of drugs, including, but not limited to etoposide, fenretinide, NBDHEX, JS-K, and RNAi constructs, or any combination thereof.

In one aspect, the therapeutic agent is an agent capable of mediating GSTM4 specific RNA interference. RNA interference (RNAi) is used to decrease the expression of GSTM4 in Ewing's sarcoma cells. Small interfering RNAs (siRNA) are dsRNAs that direct the degradation of their corresponding mRNA targets by an endonuclease complex, commonly referred to as an RNA-induced silencing complex (RISC). The RISC mediates cleavage of single-stranded RNA having sequence complementary to the antisense strand of the siRNA duplex. Cleavage of the target RNA disrupts translation of the mRNA into an active protein, thereby decreasing the overall expression of the gene, i.e., the GSTM4 gene.

RNAi can be used to interfere with gene expression in mammals. siRNAs may be administered to a cell, thereby initiating the RNAi effect against the target gene in the cell. The siRNAs may comprise any single self-complementary RNA strand or two complementary RNA strands. The RNA may be introduced in an amount which allows delivery of at least one copy per cell. Higher doses, e.g., at least 5, 10, 100, 500 or 1000 copies per cell, of double-stranded material may yield more effective inhibition; lower doses may also be useful for specific applications. Inhibition is sequence-specific in that nucleotide sequences corresponding to the duplex region of the RNA are targeted for genetic inhibition. The RNA molecule may be at least 10, 12, 15, 20, 21, 22, 23, 24, 25, 30, nucleotides in length.

siRNA can be introduced directly into a cell to mediate RNA interference. Many methods have been developed to make siRNA, e.g., chemical synthesis or in vitro transcription. Once made, the siRNAs are introduced into cells via transient transfection. A number of expression vectors have also been developed to continually express siRNAs in transiently and stably infected mammalian cells. See, e.g., Brummelkamp et al., *Science*, 296, 550 553 (2002); Sui et al., *PNAS*, 99(6),5515-5520 (2002); Paul et al., *Nature Biotechnol.*, 20, 505-508 (2002). The vectors may be delivered to a cell using a retrovirus, for example. Some of these vectors have been engineered to express small hairpin RNAs ("shRNAs"), which are processed in vivo into siRNA-like molecules capable of carrying out gene-specific silencing. Another type of siRNA expression vector encodes the sense and antisense siRNA strands under control of separate pol III promoters. See Miyagishi and Taira, *Nature Biotechnol.*, 20, 497-500 (2002). The siRNA strands from this vector, like the shRNAs of the other vectors, have 3' thymidine termination signals.

In one embodiment, the therapeutic agent capable of mediating GSTM4 specific RNA interference includes, but is not limited to, RNAi constructs selected from: EF-2-RNAi; EF-4-RNAi; GSTM4-4-RNAi; and GSTM4-5-RNAi, or any combination thereof. In one embodiment, the RNAi constructs are administered to a patient in a pharmaceutically effective amount. In one embodiment, the RNAi constructs are administered to a patient in a pharmaceutically acceptable carrier.

In one aspect, suitable GST-inhibitors are employed to prevent GSTM4 expression or activation. GST-inhibitors have been described in the art. See Flatgaard et al., *Cancer Chemother. Pharmacol.* 33:63 (1993); Lyttle et al., *J. Med. Chem.* 37: 189 (1994); and U.S. Pat. No. 5,763,570. These inhibitors were shown to potentiate the cytotoxic effect of numerous anticancer drugs in different cell lines and animal models. See Morgan et al., *Cancer Chemother. Pharmacol.*, 37, 363 (1996); and U.S. Pat. Nos. 5,763,570, 5,767,086, and 5,955,432. GST-inhibitors can also block the interaction between GSTPI-I and JNK, activate downstream signaling pathways, and cause an early restoration in peripheral blood cells in an animal models for chemotherapy-induced mylosuppression. See U.S. Pat. Nos. 5,767,086 and 5,955,432. Bivalent inhibitors capable of binding to more than one GST monomer are also contemplated by the present technology. See U.S. Pat Application No. 2005/0004038 A 1. Various methods of screening for GST-inhibitors are also known in the art. See U.S. Pat. No. 5,968,737.

In one embodiment, the activity of the GSTM4 protein is blocked through the action of a GST-inhibitor that acts as a therapeutic drug, a prodrug, a pro-apoptotic drug, or any other mechanism suitable for inhibiting the activity of GSTM4. For example, NBDHEX can inhibit GSTM4 via the inhibition of glutathione transferase P1-1 and complexes thereof. In another embodiment, the activity of the GSTM4 protein is blocked through the action of a GST-inhibitor that acts as a prodrug via release of nitric oxide following a reaction with GSTs, i.e., JS-K. Accordingly, NBDHEX, JS-K, and other suitable GST-inhibitors, prevent GSTM4 activation, thereby preventing the oncogenic transformation of Ewing's sarcoma in these cells. Thus, in one embodiment, the therapeutic agent is a GST-inhibitor.

In one aspect, one or more of the drugs, e.g., NBDHEX, JS-K, or an RNAi construct, or any combination thereof, are administered to a Ewing's sarcoma patient. In one embodiment, one or more of the drugs are administered to a patient prior to chemotherapeutic treatment. In one embodiment, one or more of the drugs are administered to a patient undergoing chemotherapeutic treatment.

In one aspect, chemotherapeutic agents are administered to a patient with Ewing's sarcoma after it has been determined that the patient is a candidate for treatment with GST-inhibitors or a GST-activated prodrug. In one embodiment, chemotherapeutic agents are administered to a subject, in combination with, or subsequent to, treatment with one or more GST-inhibitors or GST-activated prodrugs. In one embodiment, chemotherapeutic agents include, but are not limited to, etoposide, fenretinide, vincristin, doxorubicin, cyclophosphamide, ifosfamide, topotecan, irinotecan, and temozolomide. In one embodiment, the chemotherapeutic agent'administered in combination with a GST-inhibitor or GST-activated prodrug, is etoposide. In one embodiment the chemotherapeutic agent administered subsequent to a GST-inhibitor is etoposide. In one embodiment, the chemotherapeutic agent administered in combination with a GST-inhibitor or GST-activated prodrug is fenretinide. In one embodiment, the chemotherapeutic agent administered subsequent to a GST-inhibitor or GST-activated prodrug is fenretinide.

In one aspect, the drug and chemotherapeutic agents, alone or in combination, are administered to a patient in an effective amount, i.e., a therapeutically effective dose. A therapeutic dose may vary depending upon the type of therapeutic agent, route of administration, and dosage form. Dosage unit forms generally contain between from about 1 mg to about 500 mg of an active ingredient. The preferred composition or compositions is a formulation that exhibits a high therapeutic index. The therapeutic index is the dose ratio between toxic and therapeutic effects which can be expressed as the ratio between LD50 and ED50. The LD50 is the dose lethal to 50% of the population and the ED50 is the dose therapeutically effective in 50% of the population. The LD50 and ED50 are determined by standard pharmaceutical procedures in animal cell cultures or experimental animals.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation.

In the compositions for treating Ewing's sarcoma described herein, the therapeutically effective amount of the agent can range from about 0.001 mg/kg to about 30 mg/kg body weight of the subject. In some embodiments, the therapeutically effective amount of the agent can range from about 0.05 mg/kg to about 30 mg/kg, from about 0.1 mg/kg to about 30 mg/kg, from about 1 mg/kg to about 25 mg/kg, from about 1 mg/kg to about 20 mg/kg, or from about 1 or 2 mg/kg to about 15 mg/kg.

In one embodiment, etoposide is administered at a concentration between about 0.001-30, 0.05-30, 0.1-30, 1-30, 1-25, 1-20, 1-15, or 2-10 mg/kg body weight of the subject. In one embodiment, etoposide is administered at a concentration between about 2-10 mg/kg body weight of the subject. In one embodiment, etoposide is administered at a concentration between about 7 mg/kg body weight of the subject. In one embodiment, fenretinide is administered at a concentration between about 0.001-30, 0.05-30, 0.1-30, 1-30, 1-25, 1-20, 1-15, or 2-10 mg/kg body weight of the subject. In one embodiment, fenretinide is administered at a concentration between about 2-10 mg/kg body weight of the subject. In one embodiment, fenretinide is administered at a concentration between about 5 mg/kg body weight of the subject.

In one embodiment, NBDHEX is administered at a concentration between about 0.001-30, 0.05-30, 0.1-30, 1-30, 1-25, 1-20, 1-15, or 2-10 mg/kg body weight of the subject. In one embodiment, NBDHEX is administered at a concentration between about mg/kg body weight of the subject. In one embodiment, NBDHEX is administered at a concentration between about 5 mg/kg body weight of the subject. In one embodiment, JS-K is administered at a concentration between about 0.001-30, 0.05-30, 0.1-30, 1-30, 1-25, 1-20, 1-15, or 2-10 mg/kg body weight of the subject. In one embodiment, JS-K is administered at a concentration between about 2-10 mg/kg body weight of the subject. In one embodiment, JS-K is administered at a concentration between about 5 mg/kg body weight of the subject. In one embodiment, combinations of etoposide, fenretinide, NBDHEX, JS-K, and/or other GST-inhibitors and/or chemotherapeutic agents are administered to a subject for the treatment of Ewing's sarcoma and drug-resistant variations thereof.

The therapeutic agents described herein may be administered in a variety of dosage forms. In some aspects, the instant provides for compositions which may be prepared by mixing the therapeutic agents with pharmaceutically acceptable carriers, excipients, binders, diluents or the like to prevent skin cancer. Such compositions can be in the form of, for example, granules, powders, tablets, capsules, syrup, suppositories, injections, emulsions, elixirs, suspensions or solutions. The instant compositions can be formulated for various routes of administration, for example, by oral administration, by topical administration, by nasal administration, by rectal administration, subcutaneous injection, intravenous injection, intramuscular injections, or intraperitoneal injection. The following dosage forms are given by way of example and should not be construed as limiting the instant invention.

Treatment may also include administering the pharmaceutical formulations of the present disclosure in combination with other therapies. For example, the therapeutic agents, compounds, treatments, therapies, drugs, and/or pharmaceutical formulations, of the present disclosure may be administered before, during, or after a surgical procedure and/or radiation therapy. The compounds described herein can also be administered in conjunction with other anti-cancer drugs. By anticancer drugs is meant those agents which are used for the treatment of malignancies and cancerous growths by those of skill in the art such as oncologists or other physicians. Thus, anti-cancer drugs and compounds disclosed herein may be administered simultaneously, separately or sequentially. Appropriate combinations and administration regimes can be determined by those of skill in the oncology and medicine arts.

EXAMPLES

The present disclosure is further illustrated by the following examples, which should not be construed as limiting in any way. The following is a description of the materials and methods used throughout the examples.

Ewing's sarcoma cell lines. Patient-derived Ewing's sarcoma cell lines: A673; TC71; and EWS502, were employed for the following experiments.

Transcriptional profiling. All GSTM4 transcriptional profiling data was extracted from Smith, R., et al. *Cancer Cell*, 9, 405-416 (2006); and Kinsey, M., et al., *Mol Cancer Res*, 4, 851-859 (2006).

Non-human statistical analysis. In all FIGs and relevant results shown below, columns indicate the mean of duplicate or triplicate samples, and error bars indicate the standard deviation. Asterisks (*) indicate a $p<0.05$.

Luciferase assays and nucleotide constructs. Luciferase assays were performed using either a pGL3-promoter luciferase vector (Promega Corp., Madison, Wis.) containing the GSTM4 GGAA-microsatellite vector or an empty vector, or co-transfection of each into TC71 Ewing's sarcoma cells with the EWS/FLI RNAi construct (EF-2-RNAi). Co-transfection into HEK293 cells was also performed using an EWS/FLI cDNA expression vector. Negative control constructs (luc-RNAi) were employed as demonstrated in the examples below. Luciferase activities were determined as previously described in Gangwal, K., et al. *Proc Natl Acad Sci USA*, 105, 10149-10154 (2008).

Chromatin immunoprecipitation. Chromatin immunoprecipitation experiments were generally performed as described in Gangwal et al., (2008). The GGAA-microsatellite-containing region of the GSTM4 promoter from A673 cells was immunoprecipitated using α-FLI (which recognizes EWS/FLI), α-ETS1, or α-ELK1 antibodies. See Gangwal et al., (2008). The data is shown as fold-enrichment of the average enrichment of two negative controls. The mean standard error is indicated by error bars for 2-5 independent experiments.

Growth assays. Cell growth assays were performed as indicated. See Lessnick, S. L., et al., *Cancer Cell*, 1, 393-401 (2002). The assays employed Ewing's sarcoma cells (A673 or EWS502) infected with retroviral RNAi constructs and selected for using puromycin.

Soft agar assays. Soft agar assays were performed using Ewing's sarcoma cell lines infected with retroviral RNAi constructs and selected for using puromycin, as described in Kinsey, M., et al., *Mol Cancer Res.*, 4, 851-859 (2006).

Chemotherapeutic sensitivity assays. The sensitivity of Ewing's sarcoma cells to chemotherapeutic agents was determined via the following experimental procedures. The indicated Ewing's sarcoma cells were seeded at a density of $2 \times 10^4$ cells/well in 24-well plates on day-0. On day 1, cells were incubated with varying concentrations of the indicated drug or drugs for 3 days. Subsequently, MTT cell proliferation assays were performed according to the manufacturer's instructions (Cayman Chemical Company, Ann Arbor, Mich.).

Immunostaining and survival determination study. Forty four cases of morphologically-confirmed Ewing's sarcoma pretreatment primary tumor samples were obtained from the University of Michigan Medical Center Department of Pathology. The samples were analyzed by tissue microarray (TMA) via double immunofluorescence staining for a Ewing's sarcoma marker CD99, and GSTM4. Ab-27271 (rabbit polyclonal antibody, 1:100; Abcam, Cambridge, Mass.) was employed as the anti-CD99 antibody, and Ab-49484 (mouse monoclonal antibody, 1:80; Abcam, Cambridge, Mass.) was employed as the anti-GSTM4 antibody. See Camp, R. L., et al., *J Clin Oncol*, 26, 5630-5637 (2008).

Automated image acquisition and analysis. The AQUA system (HistoRx, New Haven, Conn.) was used for automated image acquisition and analysis. Briefly, images of each TMA core were captured with an Olympus BX51 microscope at different extinction/emission wavelengths. Within each TMA spot, the area of tumor was distinguished from stromal and necrotic areas by creating a tumor specific mask from the CD99 staining pattern, which was visualized using the Alexa Fluor 555 signal. Within the masked region, the fluorescence pixel intensity of the GSTM4 protein/antibody complex was obtained from the Cy5 signal and reported as pixel intensity from 0-3000. In cases where multiple primary pretreatment tumor samples were present, the average values from each sample was used. See Camp, R. L., et al., (2008).

Patient stratification and statistical analysis. Patients were stratified into two groups, those with relatively low level GSTM4 expression (0-1000; n=10), and those with relatively high level GSTM4 expression (1000-3000; n=34). The data was plotted using Kaplan-Meier stratified curves per outcome data from the University of Michigan. Cox proportional hazards models were employed using methods as described in Andersen, P. K., and Gill, R. D., *Ann Stat*, 10, 1100-1120 (1982). Statistical regression determinations were compiled using the methods described in Grambsch, P. M., and Therneau, T. M., *Biometrika*, 81, 515-526 (1994). All statistical analyses, including "survival" package, were performed using R 2.8.0 statistical software (The R Foundation for Statistical Computing, Vienna, Austria).

Example 1

GSTM4 is Regulated by EWS/FLI Binding to a GGAA-Microsatellite in the GSTM4 Promoter To evaluate the role of EWS/FLI in regulating GSTM4, we first extracted the GSTM4 data from previous transcriptional profiling studies. See Kinsey, M., et al., (2006); Smith et al., (2006). In these studies, two different retroviral RNAi constructs targeting the 3' UTR of endogenous EWS/FLI (EF-2-RNAi and EF-4-RNAi) were introduced into patient-derived Ewing's sarcoma cell lines A673, TC71, and EWS502, and were compared to a similar RNAi construct targeting the luciferase gene (luc-RNAi) as a negative control (not present in the employed cells). As shown in FIG. 1a, it was determined that decreased EWS/FLI resulted in reduced levels of GSTM4 mRNA levels in Ewing's sarcoma cell lines (additional data not shown). As shown in FIG. 1b, this result was confirmed using quantitative RT-PCR ("qRT-PCR"), in which decreased levels of EWS/FLI resulted in an approximately 80% decrease in GSTM4 expression.

FIG. 1c demonstrates that direct inspection of the GSTM4 promoter revealed the presence of a GGAA-microsatellite, consisting of 18 GGAA repeats. We have previously demonstrated that a GGAA-microsatellite regulates the NR0B1 gene in Ewing's sarcoma cells, and that EWS/FLI is capable of binding GGAA-microsatellites in vitro as well as in vivo. See Gangwal, K. and Lessnick, S. L., *Cell Cycle*, 7, 3127-32 (2008); Gangwal et al., (2008). To determine whether the GGAA-microsatellite in the GSTM4 promoter is an EWS/FLI-response element, we cloned the element upstream of a minimal promoter and a luciferase reporter cDNA. The GGAA construct was EWS/FLI-responsive in TC71 Ewing's sarcoma cells, as demonstrated by relatively high levels of luciferase activity when co-infected with an ERG-RNAi negative control vector. Further, as shown in FIG. 1d, an ~85% reduction in luciferase reporter activity was observed when EWS/FLI expression was decreased using an EWS/FLI RNAi construct ("EF-2-RNAi"). As shown in FIG. 1e, in complementary experiments, we found that co-transfection of the luciferase reporter with an EWS/FLI cDNA, in HEK293 cells, resulted in an 9-fold stimulation as compared to co-transfection with an empty vector.

To determine if EWS/FLI occupied the GSTM4 promoter in vivo, we performed directed chromatin immunoprecipitation experiments ("ChIP") using antibodies and conditions as previously described. Gangwal et al., (2008). FIG. 1f demonstrates that immunoprecipitation of EWS/FLI concomitantly immunoprecipitated the GSTM4 microsatellite region, while two other ETS family members, ETS1 and ELK1, were not immunoprecipitated. Taken together, these data support the conclusion that GSTM4 is unregulated in Ewing's sarcoma cells by direct binding of EWS/FLI to the GGAA-microsatellite in the GSTM4 promoter.

Example 2

GSTM4 is Necessary for Oncogenic Transformation of Ewing's Sarcoma Cells

Figure 2:
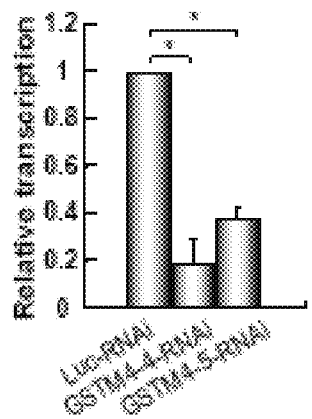
FIG. 2a is a graph showing quantitative RT-PCR results for GSTM4 RNA levels from RNAi infected A673 Ewing's sarcoma cells.
FIG. 2b is a graph demonstrating the growth potential for RNAi infected Ewing's sarcoma cells.
FIG. 2c is a graph representing results from soft agar assays with Ewing's sarcoma cells.
Figure 2:
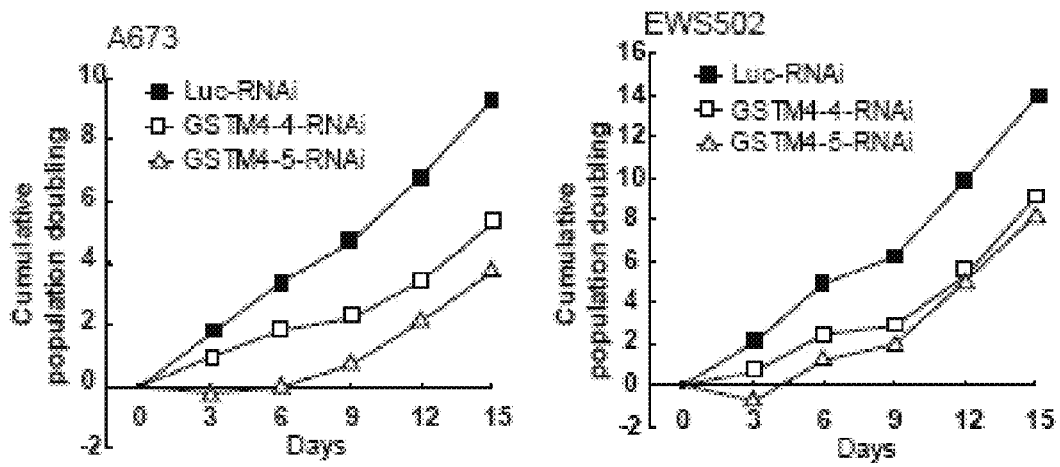
Figure 2:
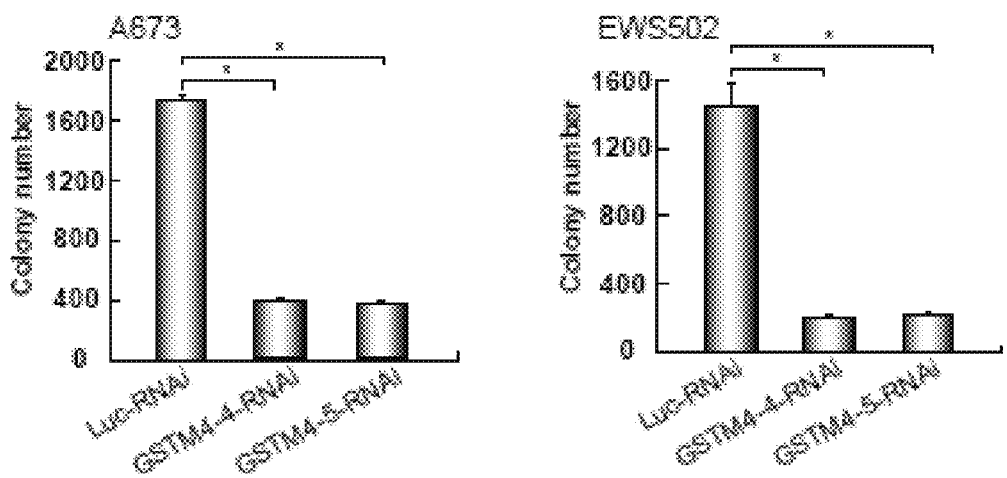

This example demonstrates that GSTM4 has a functional role in the ontogenesis Ewing's sarcoma. First, it was investigated whether GSTM4 is required for maintaining the oncogenic phenotype of Ewing's sarcoma via loss-of-function analysis. We designed shRNAs against the 3' UTR of GSTM4 and cloned them into retroviral constructs, GSTM4-4-RNAi and GSTM4-5-RNAi. As shown in FIG. 2a, when compared to negative controls (empty vector infection), qRT-PCR analysis of polyclonal infected and selected populations of A673 Ewing's sarcoma cells demonstrated efficient reduction of endogenous GSTM4 mRNA levels. FIG. 2b demonstrates that GSTM4 depleted cells proliferated more slowly than control cells in tissue culture. FIG. 2c demonstrates that decreased GSTM4 expression results in a diminished anchorage-independent growth in soft agar experiments. To this end, decreased GSTM4 expression resulted in a significant reduction in oncogenic transformation. The fact that two different retroviral RNAi constructs showed nearly identical phenotypes in two different patient-derived Ewing's sarcoma cell lines suggested that these results are specific for reduced GSTM4 expression. These results demonstrate that ongoing GSTM4 expression is required for the transformed phenotype of Ewing's sarcoma. Further, GSTM4 was depleted from U2OS osteosarcoma cells and it was determined that cell growth and colony formation were not affected (data not shown). Accordingly, GSTM4 is specific to oncogenic transformation in Ewing's sarcoma cells.

Example 3

Figure 3:
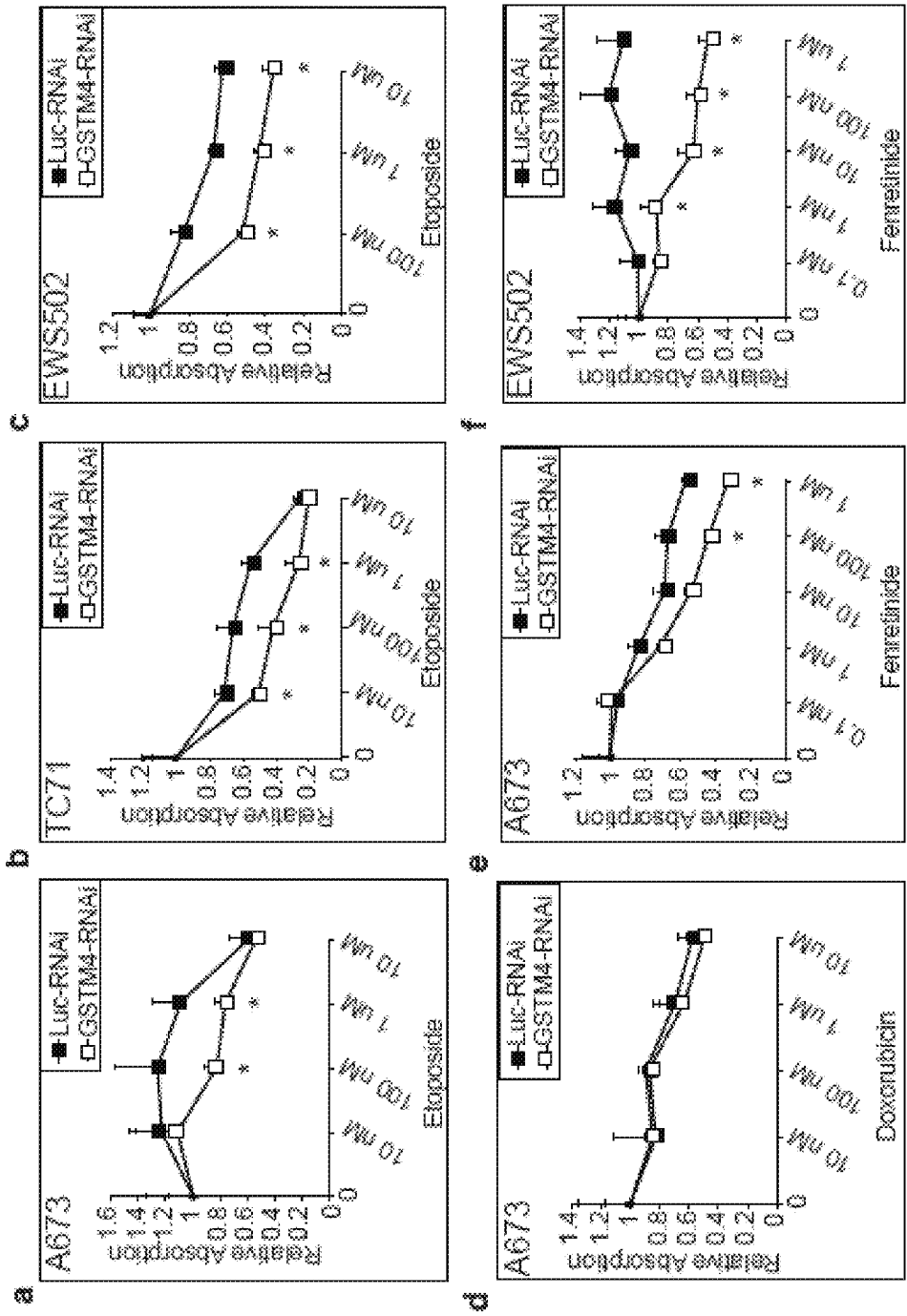
FIGS. 3a to 3c are graphs showing that Ewing's sarcoma cells with decreased levels of GSTM4 are sensitive to etoposide.
FIG. 3d is a graph showing that Ewing's sarcoma cells with decreased levels of GSTM4 are not sensitive to doxorubicin.
FIGS. 3e to 3f are graphs showing that Ewing's sarcoma cells with decreased levels of GSTM4 are sensitive to fenretinide.

Depletion of GSTM4 Increases the Sensitivity of Ewing's Sarcoma Cells to Chemotherapeutic Agents—GSTM4 is a Valid Biomarker for Drug Resistance To test whether GSTM4 contributed to the chemotherapeutic resistance profile of Ewing's sarcoma, wild-type (luc-RNAi) and reduced GSTM4 (GSTM4-4-RNAi) cells were treated with increasing dosages of chemotherapeutic drugs and tested using MTT survival assays. The chemotherapeutic agents that were tested included etoposide, doxorubicin, and melphalan. FIGS. 3a-c demonstrate that decreased levels of GSTM4 resulted in an increase in sensitivity to etoposide when compared to controls.

It was further determined that GSTM4 can alter the sensitivity of Ewing's sarcoma cells for fenretinide. FIG. 3e-f demonstrate that Ewing's sarcoma cells with reduced GSTM4 levels, via GSTM4-4-RNAi, were more sensitive to fenretinide than control cells. It was further determined that decreased GSTM4 levels can change intracellular redox potential. However, GSTM4 depleted A673 cells only demonstrated a minimal increase in redox potential (data not shown). The drug-sensitivity data demonstrates that reduction of GSTM4 levels confers increased sensitivity to specific cytotoxic agents in Ewing's sarcoma cells. This data shows that inhibition of GSTM4 activity can be used in combination with chemotherapy to increase therapeutic responses in Ewing's sarcoma.

Example 4

Figure 4:
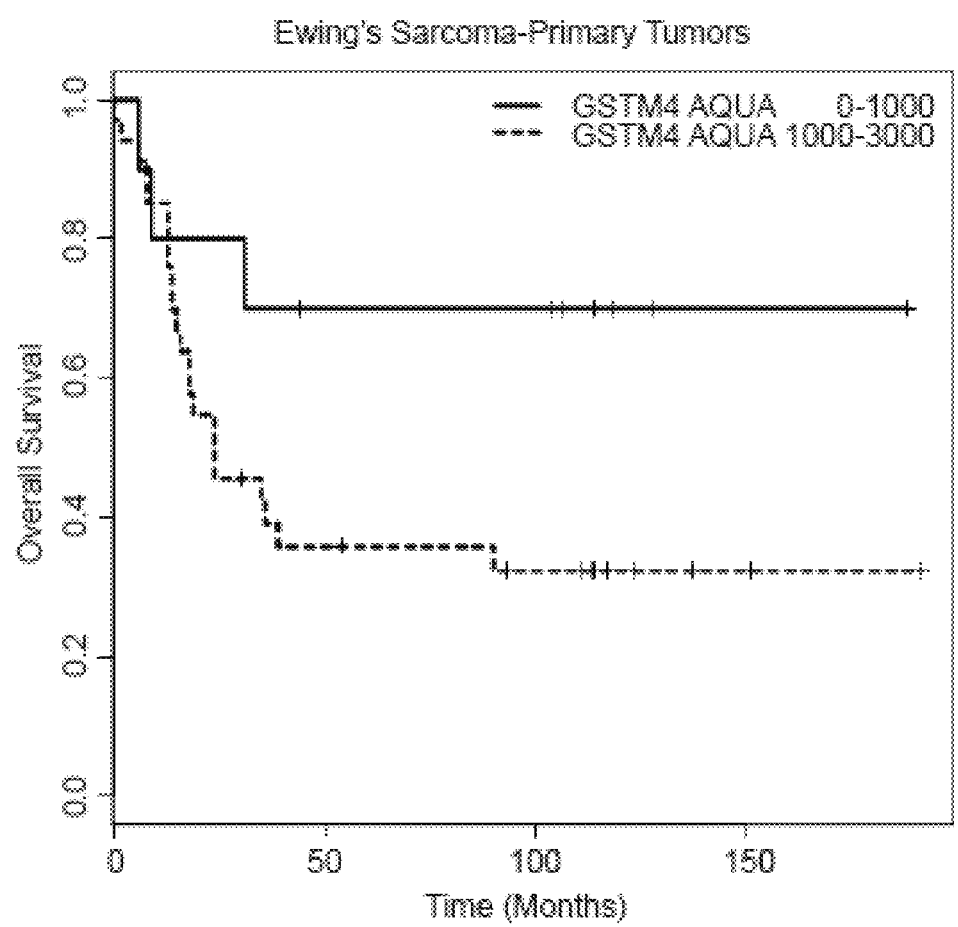
FIG. 4 is a graph showing the overall survival of patients with Ewing's sarcoma primary tumors. The graph represents the Kaplan-Meier analysis showing that high GSTM4 levels are linked to a poor survival prognosis.

GSTM4 Expression in Tumors Correlates with Overall Survival in Ewing's Sarcoma Patients TMA was performed using Ewing's sarcoma tumor specimens stained for GSTM4 (FIG. 4). The results were determined using an AQUA system semi-quantitative analysis as described in Camp, R. L., et al., (2008). It was determined that patients with higher GSTM4 levels in primary tumors had lower overall survival rates (FIG. 4). However, due to a small sample size, the results were not statistically significant (p=0.054). Accordingly, increased GSTM4 levels correlate with therapeutic resistance and decreased survival in Ewing's sarcoma patients. Consequently, when combined with chemotherapeutic agents, GSTM4 inhibitors can provide increased efficacy in treating Ewing's sarcoma.

Example 5

Figure 5:
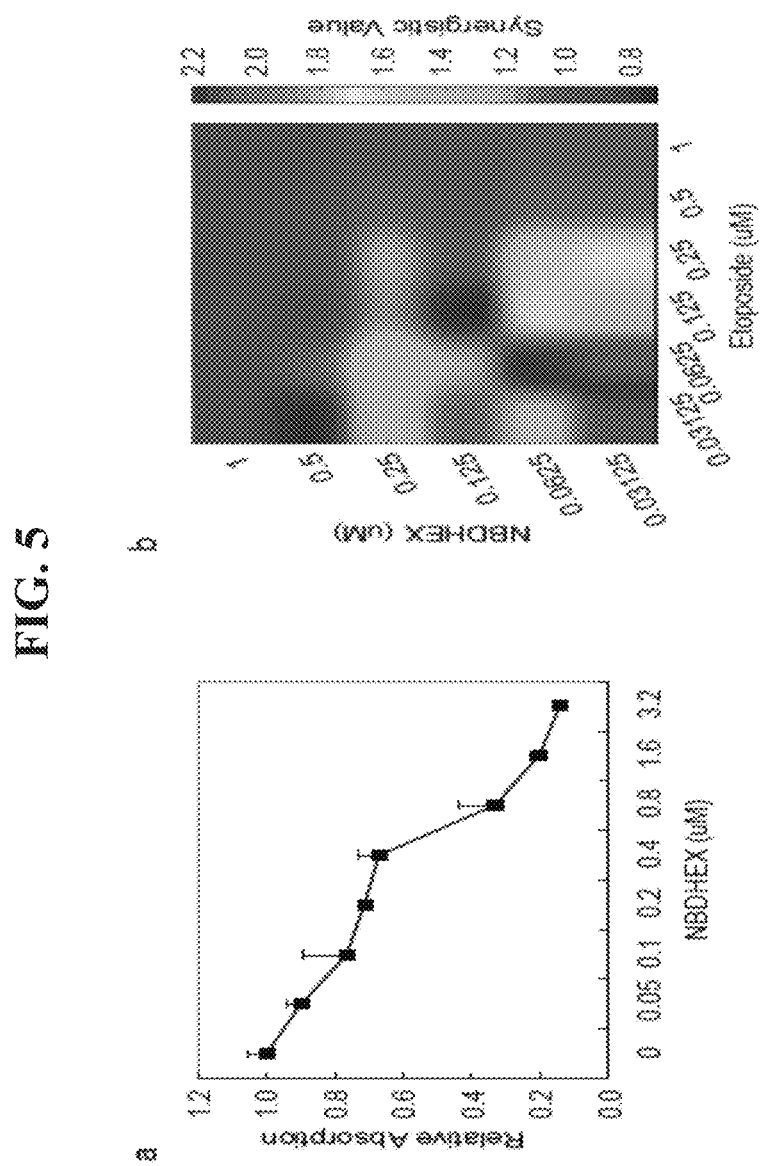
FIG. 5a is a graph showing that the GST-inhibitor NBD-HEX is effective to kill Ewing's sarcoma cells.
FIG. 5b is a graph showing that the GST-inhibitor NBDHEX has synergistic effect with etoposide to Ewing's sarcoma cells.

GSTM4 Inhibitors Increase the Sensitivity of Ewing's Sarcoma Cells to Chemotherapeutic Agents Ewing's sarcoma cells (A673) were treated with NBD-HEX, which was synthesized as described in *JBC* 2005, 26397-26405. The A673 cells were seeded at a density of $2\times10^4$ cells/well in 24-well plate on day 0. On day 1, cells were treated with increasing concentrations of NBDHEX (0, 0.05, 0.1, 0.2, 0.4, 0.8, 1.6, or 3.2 µM) or a negative control for 3 days. MTT cell proliferation assays showed that NBDHEX was able to effectively inhibit A673 cell proliferation at an $IC_{50}$ of 0.5 µM (FIG. 5a).

Ewing's sarcoma cells (A673) were also treated with NBDHEX and etoposide (Sigma). The A673 cells were seeded at a density of $2\times10^4$ cells/well in 24-well plate on day 0. On day 1, cells were incubated with increasing concentrations of NBDHEX (0.03125, 0.0625, 0.125, 0.25, 0.5, or 1 µM) or etoposide (0.03125, 0.0625, 0.125, 0.25, 0.5, or 1 µM) or NBDHEX and etoposide for 3 days. MTT cell proliferation assays demonstrate that low doses (0.03125 or 0.0625 µM) of NBDHEX combined with etoposide inhibits A673 cell proliferation more effectively than NBDHEX or etoposide alone. Subsequently, a synergistic effect additive model was employed to determine whether cytotoxic synergy existed between NBDHEX and etoposide. As shown in FIG. 5b, there is a dose-dependent synergy between NBDHEX and etoposide (warmer colors represent greater synergy). These results demonstrate that combining GSTM4 inhibition with chemotherapeutic agents, i.e., etoposide, is a novel therapeutic approach for treating Ewing's sarcoma.

Figure 6:
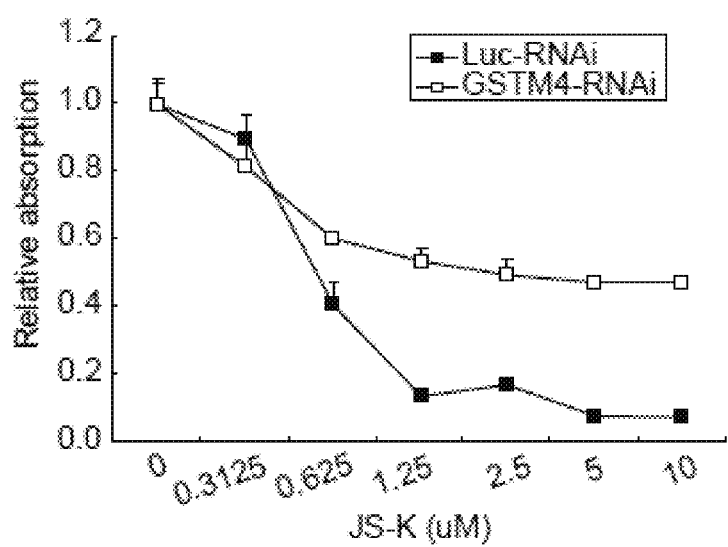
FIG. 6 is a graph showing that the GST-activated prodrug JS-K is less effective in killing Ewing's sarcoma cells with decreased GSTM4 levels compared to controls.

JS-K (provided by Dr. Paul Shami at the University of Utah) is a GST-activated prodrug with potent anti-neoplastic activity. A673, Ewing's sarcoma, cells with wild type (Luc-RNAi) or decreased GSTM4 levels (GSTM4-RNAi infected cells) were seeded in 24-well plates at a density of $2\times10^4$ cells/well. GSTM4 decreased cells or negative controls were treated with increasing concentrations of JS-K (0, 0.3125, 0.625, 1.25, 2.5, 5, or 10 µM) for 72 hours, followed by an MTT cell viability analysis. As shown in FIG. 6, Ewing's sarcoma cells with decreased GSTM4 levels are less sensitive to JS-K than control cells. This result indicates that JS-K is a novel treatment for Ewing's sarcoma patients.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present disclosure has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

SEQUENCE LISTING

<160> NUMBER OF SEQ ID NOS: 3

<210> SEQ ID NO 1
<211> LENGTH: 350
<212> TYPE: DNA
<213> ORGANISM: Homo sapiens

<400> SEQUENCE: 1

```
aaagaaagaa agaaaagaaa gaaagaaaga aagaaagaaa gaaagaaaga aagaaagaaa        60
agaaagaaag aaagaaagaa agaaagaaag aaagaaagaa agaaagaaag gaaagaaaga       120
aaagaaagaa agaaaggaaa gaaagaaaga aagaaggaag gaaggaagga aggaaggaag       180
gaaggaaggg aaggaaggaa ggaaggaagg aaggaaggaa ggaaggaagg atacccagaa       240
gcttctaaaa tgaggaaagc acagataatc tggtggacca tccaggaagg ataattgatt       300
tctctcatac aagatgcaat tcccatagta ggaataaaac aagatatatg                 350
```

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2

```
tctgccctac ttgattgatg g                                                 21
```

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3

```
tgattggaga cgtccatagc c                                                 21
```

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for determining a prognosis of a patient with Ewing's sarcoma, said method comprising:
   (a) determining the level of expression of a gene encoding glutathione S-transferase mu 4 (GSTM4) in a sample of Ewing's sarcoma cells acquired from the patient; and
   (b) determining the patient has a relatively worse prognosis if the level of expression determined is equal to or greater than a reference level at or above which there is a statistically significant negative correlation between the level of expression of the gene in a sample of Ewing's sarcoma acquired from individuals and the individuals' overall survival; or
   (c) determining the patient has a relatively better prognosis if the level of expression determined is less than a reference level at or above which there is a statistically significant negative correlation between the level of expression of the gene in Ewing's sarcomas acquired from individuals and the individuals' overall survival.

2. The method of claim 1, wherein the level of expression of a gene encoding GSTM4 in the sample is determined by measuring the amount of RNA encoding GSTM4.

3. The method of claim 2, wherein the amount of RNA encoding GSTM4 is measured after amplification of the RNA in the sample using reverse transcription-polymerase chain reaction (RT-PCR).

4. The method of claim 2, wherein the measurement of the amount of RNA in the sample employs a detectably labeled primer or probe.

5. The method of claim 1, wherein the level of expression of a gene encoding GSTM4 in the sample is determined by measuring the amount of GSTM4 protein.

6. The method of claim 5, wherein the amount of GSTM4 protein is measured using an immunoassay.

7. The method of claim 6, wherein said immunoassay is selected from the group consisting of an ELISA, a Western blot assay, and an immunohistochemical assay.

8. The method of claim 1, wherein said sample of Ewing's sarcoma cells acquired from the patient is acquired by biopsy.

9. The method of claim 1, wherein if the patient is determined to have a relatively worse prognosis the patient is more likely to have a relatively decreased overall survival as compared to a patient determined to have a relatively better prognosis.

10. The method of claim 1, wherein if the patient is determined to have a relatively better prognosis the patient is more likely to have a relatively increased overall survival as compared to a patient determined to have a relatively poor prognosis.

11. The method of claim 1, wherein if the patient is determined to have a relatively worse prognosis the patient is less likely to respond to treatment with a chemotherapeutic agent selected from etoposide and fenretinide.

12. The method of claim 1, wherein if the patient is determined to have a relatively better prognosis the patient is more likely to respond to treatment with a chemotherapeutic agent selected from etoposide and fenretinide.

* * * * *